United States Patent [19]

Walsh et al.

[11] 4,254,135
[45] Mar. 3, 1981

[54] 3-AMINO-4-HYDROXYPYRROLIDINES

[75] Inventors: David A. Walsh; Dwight A. Shamblee, both of Richmond, Va.

[73] Assignee: A. H. Robins Company, Inc., Richmond, Va.

[21] Appl. No.: 85,361

[22] Filed: Oct. 16, 1979

Related U.S. Application Data

[63] Continuation-in-part of Ser. No. 25,416, Mar. 30, 1979, abandoned.

[51] Int. Cl.³ .................. C07D 207/14; A61K 31/40
[52] U.S. Cl. ............................ 424/274; 260/326.33; 260/326.46; 260/326.47; 260/326.5 R; 260/326.5 B; 260/326.5 C; 260/326.5 L
[58] Field of Search ............... 260/326.47, 326.5 C, 260/326.5 L, 326.33, 326.46; 424/274

[56] References Cited
U.S. PATENT DOCUMENTS 3,691,198  9/1972  Brown et al. ................. 260/326.8

OTHER PUBLICATIONS

Beereboom et al., J. Org. Chem., vol. 30, pp. 2334-2342 (1965).

Primary Examiner—Mary C. Lee

[57] ABSTRACT

Cis and trans 3-amino-4-hydroxypyrrolidines and derivatives thereof are disclosed having the formula:

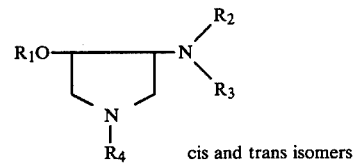

cis and trans isomers wherein $R_1$ is hydrogen, loweralkyl or phenylcarbonyl; $R_2$ is hydrogen, loweralkyl, lowercycloalkyl, phenyl or phenylloweralkyl; $R_3$ is hydrogen, loweralkyl, phenylloweralkyl, phenylcarbonyl, diphenylmethyl, 5-yl-10,11-dihydro-5H-dibenzo[a,d]cycloheptene or naphthylcarbonyl; $R_4$ is hydrogen, loweralkyl, phenylloweralkyl or lowercycloalkyl; phenyl is optionally substituted and acid addition salts thereof. The compounds have antidepressant activity and methods and pharmaceutical compositions for use thereof are disclosed.

93 Claims, No Drawings

3-AMINO-4-HYDROXYPYRROLIDINES

The present application is a continuation-in-part application of copending application Ser. No. 025,416 filed Mar. 30, 1979 now abandoned.

BACKGROUND OF THE INVENTION

1. Field of Invention

The present invention relates to certain novel cis and trans-3-amino-4-hydroxypyrrolidines and novel methods for making and novel pharmaceutical use therefor. More particularly, the invention relates to novel 3-amino-4-hydroxypyrrolidines and derivatives thereof which have potent activity in the treatment of depression in animals and novel methods of making the compounds.

2. Description of the Prior Art

Compounds of the present invention have not heretofore been available. The stereochemistry of anisomycin which has paramethoxy-phenylalkyl substitution in the 2-position of 3-amino-4-hydroxypyrrolidine, which the compounds of the present invention do not have, was studied by Beereboom, J. J. et al, in J. Org. Chem. 30, 2334–42 (1965).

SUMMARY OF INVENTION

The present invention provides novel cis and trans 3-amino-4-hydroxypyrrolidines, novel procedures of preparation and novel methods of treating depression in mammals and pharmaceutical compositions therefor.

The novel compounds of the invention are represented by the following general structure formula:

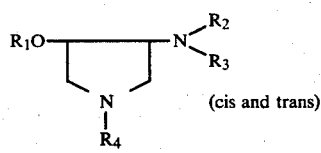

Formula I (cis and trans)

wherein;

$R_1$ is hydrogen, loweralkyl or phenylcarbonyl, $R_2$ is hydrogen, loweralkyl, lowercycloalkyl, phenyl or phenylloweralkyl, $R_3$ is hydrogen, loweralkyl, phenyl-loweralkyl, phenylcarbonyl, diphenylmethyl, -5-yl-10,11-dihydro-5H-dibenzo [a,d]cyclohetpene, or naphthyl-carbonyl, $R_4$ is hydrogen, loweralkyl, phenyl-loweralkyl or lower cycloalkyl, phenyl is unsubstituted phenyl, or phenyl substituted by 1 to 3 radicals selected from halogen, alkyl, loweralkoxy, trifluoromethyl, benzyloxy, nitro, amino, acetamido and hydroxy, and the pharmaceutically acceptable acid addition salts thereof.

Compounds preferred for their antidepressant activity have the formula:

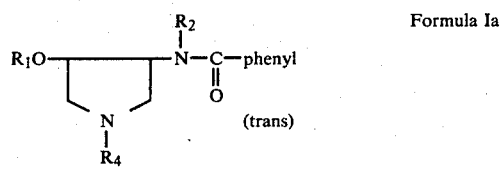

Formula Ia (trans)

wherein $R_1$, $R_4$ and phenyl are as hereinabove defined, and $R_2$ is phenyl, lower alkyl and lower cycloalkyl.

In the further definition of symbols the term "loweralkyl" includes straight and branched chain radicals containing 1 to 8 carbon atoms as, for example, methyl, ethyl, propyl, isopropyl, n-butyl, isobutyl, tertiary butyl, amyl, isoamyl, n-hexyl, n-heptyl, and n-octyl radicals. Ethyl is a preferred loweralkyl radical. A loweralkoxy group has the formula -O-loweralkyl.

The term "lowercycloalkyl" as used herein includes primarily cyclic alkyl radicals containing three up to nine carbon atoms inclusive and encompasses such groups as cyclopropyl, cyclobutyl, cyclopentyl, ethylcyclopentyl, cyclohexyl, methylcyclohexyl, propylcyclohexyl, cycloheptyl, and cyclooctyl. The cyclohexyl radical represents a preferred cycloalkyl radical.

Antidepressant activity was shown to be present by the procedure given by Englehardt, E. L. et al, J. Med. Chem. 11, (2): 325 (1968) wherein the compounds of the present invention were administered to mice intraperitoneally and the effectiveness of the compounds in blocking depressant effects which are induced in mice by intravenous administration of 2-oxo-3-isobutyl-9,10-dimethoxy-1,2,3,4,6,7-hexahydro-11bh-benzo [a]-quinolizine(tetrabenazine) was determined. Some compounds which showed potent activity in the foregoing test are as follows:

| Example No. | Antidepressant Activity (Antitetrabenazine Test $ED_{50}$, mg/kg) |
|---|---|
| 27 | 1.1 |
| 28 | 2.9 |
| 29 | 2.7 |
| 50 | 0.3 | and are consequently among the preferred compounds of the invention which may be further identified under the preferred Formula Ia.

It is, accordingly, an object of the present invention to provide cis and trans 3-amino-4-hydroxypyrrolidines which have a high degree of antidepressant activity and methods of producing and using the compounds.

Another object is to provide a novel composition and methods for the treatment of living animals, especially mammals, for the purpose of relieving anxiety and depression.

Additional objects will be apparent to one skilled in the art and still other objects will become apparent hereinafter.

DETAILED DESCRIPTION OF THE INVENTION

The present invention encompasses the novel cis and trans isomers of 3-amino-4-hydroxypyrrolidines and derivatives thereof as set forth hereinabove in Formula I and the definitions therewith as compositions of matter and the utilization of these novel compounds in living animals for their antidepressant effect as set forth hereinabove and below.

The term "loweralkyl" as used in the specification and claims includes straight and branched chain radicals of up to eight carbon atoms inclusive and is exemplified by such groups as methyl, ethyl, propyl, isopropyl, butyl, isobutyl, tertiary butyl, amyl, isoamyl, hexyl, heptyl, octyl and the like.

By "cycloalkyl" is meant cycloalkyl radicals having 1 to 9 carbon atoms and includes such radicals as cyclopropyl, cyclobutyl, cyclopentyl, cyclohexyl and the like.

Representative of phenylloweralkyl radicals are benzyl, α-methylbenzyl, phenylethyl, phenylpropyl, phenylbutyl, and the like.

The starting materials used in preparing the novel compounds of Formula I are illustrated by preparations 2–4 which preparations may be represented by the following equation:

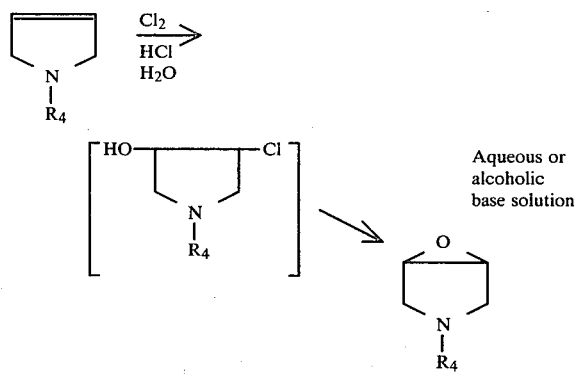

wherein $R_4$ is loweralkyl, phenylloweralkyl or cyclohexyl. The pyrrolines used in these preparations are prepared according to the procedure of U.S. Pat. No. 3,691,198 and the preparation of one new pyrroline is given in Preparation 1.

PREPARATION 1

1-Cyclohexyl-$\triangleleft^3$-pyrroline.

A solution of 5.19 kg (52.3 moles) of cyclohexylamine in 4.0 liters of benzene was heated to mild reflux (92° C.) and then the heating discontinued. To the solution was added, dropwise, 1,635 g (13.1 moles) of 1,4-dichlorobutene at a rate sufficient to maintain gentle reflux, 3 hours time being required. Heat was reapplied and the reactants were heated at reflux temperature for 18 hours. The mixture was cooled to about 50° C. and filtered to remove the hydrochloride. Carbon dioxide was bubbled into the filtrate to precipitate excess amine carbonate which was removed by filtration. Solvent was removed from the filtrate by distillation under reduced pressure and the reddish fluid residue slightly contaminated with benzene weighed 1,506 g (76% yield).

PREPARATION 2

1-Cyclohexyl-3,4-epoxyprrolidine Oxalate.

A solution of 151.3 g (1.0 mole) of N-cyclohexyl-$\triangleleft^3$-pyrroline, 100 ml of concentrated hydrochloric acid and 1.8 L of water was treated with a stream of chlorine gas until uptake ceased (~6 hrs.). The solution was washed with methylene chloride and the acidic solution was left standing overnight. The solution was then made basic with 50% sodium hydroxide and extracted with methylene chloride. The combined extracts were concentrated to give 185 g of chlorohydrin as residue. The residue was slowly poured into an ethanol solution containing 20% sodium hydroxide. The mixture was stirred for 0.5 hr and then 3.5 liters of water was added. The mixture was extracted with methylene chloride and the combined extracts were dried over anhydrous sodium sulfate and concentrated to give 154 g (92%) of amine epoxide. An NMR analysis indicates this residue is 86% epoxide and 14% 3,4-dichloro-N-cyclohexylpyrrolidine. The residue was vacuum distilled to give the epoxide as a waterwhite liquid, b.p. 71° C. at 0.6 mm. A portion of the liquid was converted to the oxalate to give a white solid, m.p. 155°–6° d when recrystallized from ethanol.

Analysis: Calculated for $C_{12}H_{19}NO_5$: C,56.02; H,7.44; N,5.44. Found: C,56.05; N,5.34.

PREPARATION 3

1-Ethyl-3,4-epoxy-pyrrolidine Oxalate.

A mixture of 61 g (0.63 mole) of 1-ethylpyrroline, 50 ml of concentrated aqueous hydrochloric acid and 600 ml of water was treated with chlorine gas for 2.5 hrs. The mixture was filtered through cotton and the filtrate was washed with two 100-ml portions of methylene chloride. The aqueous layer was made basic with 20% sodium hydroxide, heated on a steam bath for 0.5 hr and extracted with three 100-ml portions of methylene chloride. The combined extracts were dried over anhydrous sodium sulfate and concentrated and the residue vacuum distilled to give 39.4 g (56%) of the epoxide as a clear oil (b.p. 75°–90° at 28 mm). The epoxide was converted to the oxalate and the salt was recrystallized from absolute ethanol to give the white needles, m.p. 142°–4° d.

Analysis: Calculated for $C_8H_{13}NO_5$: C,47.29; H,6.45; N,6.89. Found: C,47.12; H,6.42; N,6.82.

PREPARATION 4

1-Benzyl-3,4-epoxypyrrolidine Oxalate.

A mixture of 31.8 g. (0.20 mole) of N-benzyl-$\triangleleft^3$-pyrroline, 25 l. of concentrated hydrochloric acid and 300 ml of water was treated with a stream of chlorine gas for 2 hrs. The solution was filtered and the filtrate was made basic with 20% sodium hydroxide. The basic solution was extracted with three 150 ml-portions of methylene chloride. The combined methylene chloride extracts were dried over magnesium sulfate and evaporated to give 48.5 g. of crude chlorohydrin as a dark oil. This oil was stirred with 200 ml of 20% sodium hydroxide 0.5 hr., 700 l. of water was added, and the base was extracted with four 100-ml portions of methylene chloride. The combined methylene chloride extracts were dried over magnesium sulfate and concentrated to yield 34.9 g (99%) of crude epoxide as a dark oil. The oxalate salt was prepared in 81% yield. Recrystallization from 95% ethanol gave the salt as off-white needles, m.p. 148°–49° d.

Analysis: Calculated for $C_{13}H_{15}NO_5$: C,58.86; H,5.70; N,5.28. Found: C,58.55; H,5.68; H,5.25.

Synthesis of trans-isomer compounds of Formula I which are part of the present invention and which also serve as intermediates for the preparation of other compounds of the invention was started by reacting 1-substituted-3,4-epoxypyrrolidines and appropriate amines as exemplified by the following equation:

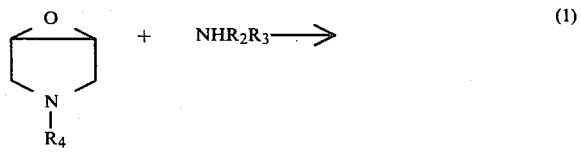

Formula IV

-continued $$\text{HO}\underset{\underset{R_4}{|}}{\overset{}{\underset{N}{\bigcirc}}}\text{NR}_2R_3$$

(trans isomers)

Formula Ib wherein $R_2$ and $R_4$ are as defined hereinabove and $R_3$ is hydrogen, loweralkyl, phenylloweralkyl, diphenylmethyl and 5-yl-10,11-dihydro-5H-dibenzo[a,d]cycloheptene.

Synthesis of cis isomers which are part of the present invention and which serve as reactions for other compounds of the invention was started by reacting trans-4-amino-1-$R_4$-3-pyrrolidinol of Formula Ib with p-chlorobenzoyl chloride to obtain trans-4-chloro-N-(1-$R_4$-4-hydroxy-3-pyrrolidinyl)benzamide which was cyclized in sulfonylchloride to form 2-(4-chlorophenyl)-5-$R_4$-5,6-dihydro-4H-pyrrolo [3,4-]oxazole hydrochloride which was then converted to cis-4-chloro-N-(1-$R_4$-4-hydroxy-3-pyrrolidinyl)benzamide as exemplified by the following equations:

(2)

(3)

In preparing compounds having further variation under Formula I, the following additional methods may be used for preparation of either trans or cis isomers as illustrated by the following equations:

(4)

(5)

(6)

(7)

(8)

-continued

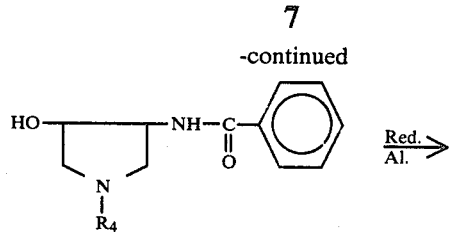

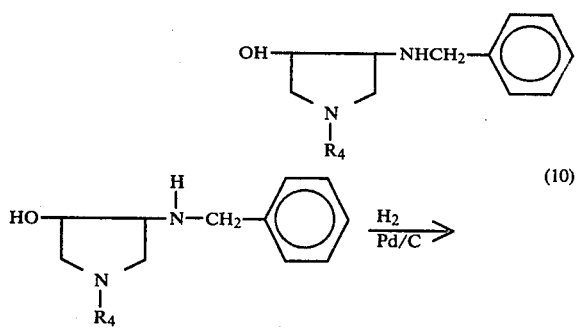

R₄ = hydrogen, lowercycloalkyl, or loweralkyl

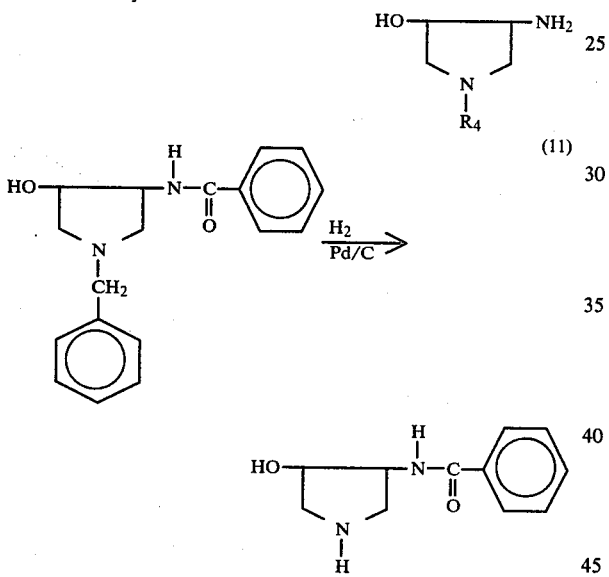

To obtain the base of a compound prepared as an acid addition salt, the salt is partitioned between saturated alkali-bicarbonate solution and methylene chloride. The methylene chloride layer is dried over sodium sulfate and concentrated to give the base as residue.

The novel compounds of the present invention and the methods for their preparation are exemplified more fully by the following illustrative examples; the scope of the invention is, however, not limited thereto. As will be readily identifiable from a consideration of the examples and the foregoing outline, many of the compounds under the scope of Formula I may be also considered as intermediates in the synthesis of other compounds of Formula I.

EXAMPLE 1

Trans-4-amino-1-cyclohexyl-3-pyrrolidinol Dimaleate.

A mixture of 16.7 g of 1-cyclohexyl-3,4-epoxypyrrolidine in ca. 100 ml of liquid ammonia was sealed in a comb and heated at 110° C. for 24 hours. After cooling and evaporation of the ammonia, some of the crystalline white powder was converted to the dimaleate salt in isopropyl alcohol, m.p. 117.0°–180.5° C. The base rapidly forms a hygroscopic carbonate salt.

Analysis: Calculated for $C_{18}H_{28}N_2O_9$: C,51.92; H,6.78; N,6.73. Found: C,52.10; H,6.76; N,6.70.

EXAMPLE 2

Trans-4-chloro-N-(1-cyclohexyl-4-hydroxy-3-pyrrolidinyl)benzamide.

A solution of 36.8 g of trans-4-amino-1-cyclohexyl-3-pyrrolidinol in 600 ml of p-dioxane was mixed with 40 g of powdered anhydrous potassium carbonate and stirred while 35.0 g of p-chlorobenzoyl chloride in 100 ml of p-dioxane was added dropwise. The mixture was stirred at room temperature for 2 hrs, then heated at reflux for 2 hrs. While still hot, 10 ml of water was added to make the precipitate granular; the mixture was filtered and the dioxane reduced to one-half volume. This solution was poured into one liter of water. The precipitate was collected and recrystallized from acetone. Yield was 60.5 g (94%), m.p. 193°–195° C.

Analysis: Calculated for $C_{17}H_{23}N_2O_2Cl$: C,63.25; H,7.18; N,8.68. Found: C,63.40; H,7.27; N,8.62.

EXAMPLE 3

Trans-N-(1-cyclohexyl-4-hydroxy-3-pyrrolidinyl)benzamide.

This compound was prepared in a manner analagous to Example 2, using 8.1 g of trans-4-amino-1-cyclohexyl-3-pyrrolidinol, 10 g of potassium carbonate and 6.2 g of benzoyl chloride. After filtration and solvent evaporation, the residue crystallized and was recrystallized from acetone. Yield was 5.8 g (45%), m.p. 154.0°–155.5° C.

Analysis: Calculated for $C_{17}H_{24}N_2O_2$: C,70.80; H,8.39; N,9.71. Found: C,70.60; H,8.48; N,9.76.

EXAMPLE 4

Trans-4-acetylamino N-(1-cyclohexyl-4-hydroxy-3-pyrrolidinyl)benzamide Hydrate (1:4).

A mixture of 9.1 g of trans-N-(1-cyclohexyl-4-hydroxy-3-pyrrolidinyl)benzamide and 8 g of powdered anhydrous potassium carbonate in 500 ml of tetrahydrofuran was cooled to 5° C. and stirred while 2.4 g of acetyl chloride in 35 ml chloroform was added dropwise. The mixture was allowed to come to room temperature and stirred for 5 hrs, then it was filtered and the solvent was evaporated under vacuum. Acetone was added; the residue crystallized; it was recrystallized from acetone. Yield was 5.2 g (50%), m.p. 209.5°–211.5° C.

Anlaysis: Calculated for $C_{76}H_{110}N_{12}O_{13}$: C,65.21; H,7.92; N,12.01. Found: C,65.17; H,7.97; N,11.83.

EXAMPLE 5

Trans-N-(1-cyclohexyl-4-hydroxy-3-pyrrolidinyl)-4-nitrobenzamide.

A solution of 1.84 g (0.01 mole) of 4-amino-1-cyclohexyl-3-pyrrolidinol in 50 ml of methylene chloride was cooled to 5° C. and 2 g of powdered, anhydrous potassium carbonate was added. The mixture was stirred while a solution of 1.86 g of p-nitrobenzoyl chloride in 20 ml of methylene chloride was added dropwise. The mixture was then allowed to warm to room temperature and was stirred for one hour. The slurry was filtered, and the residue, after solvent evaporation, crystallized immediately and was recrystallized from acetone. Yield was 3.0 g (90%), m.p. 155.5°–157.0° C.

Analysis: Calculated for $C_{17}H_{23}N_3O_4$: C,61.25; H,6.95; N,12.60. Found: C,61.06; H,6.99; N,12.47.

EXAMPLE 6

Trans-4-nitrobenzoic Acid Ester with 1-Cyclohexyl-3-{[(4-nitrophenyl)carbonyl]amino}-3-pyrrolidinol.

This compound was isolated as a side product in the preparation of trans-N-(1-cyclohexyl-4-hydroxy-3-pyrrolidinyl)-4-nitrobenzamide. It was recrystallized from acetone-EtOH; m.p. 219.5°–221.5° C.

Analysis: Calculated for $C_{24}H_{26}N_4O_7$: C,59.75; H,5.43; N,11.61. Found: C,59.96; H,5.47; N,11.67.

EXAMPLE 7

Trans-4-amino-N-(1-cyclohexyl-4-hydroxy-pyrrolidin-3-yl)benzamide.

A solution of 25 g (0.075 mole) of trans-N-(1-cyclohexyl-4-hydroxy-3-pyrrolidinyl)-4-nitrobenzamide was treated with ca. 1 g of 10% palladium on charcoal catalyst and was shaken with hydrogen at 60° in the Parr reduction apparatus until three equivalents of hydrogen were absorbed. The suspension was then cooled, filtered and the solvent evaporated at aspirator vacuum. The white granular powder remaining weighed 22.7 g, a quantitative yield. After recrystallizing from benzene-actone, the product melted at 155.5°–1155.6° C.

Analysis: Calculated for $C_{17}H_{25}N_3O_2$: C,67.30; H,8.31; N,13.85. Found: C,67.24; N,8.32; N,13.63.

EXAMPLE 8

Trans-1-cyclohexyl-4-phenylmethylamino-3-pyrrolidinol Dimaleate.

A mixture of 3.4 g of 1-cyclohexyl-3,4-epoxypyrrolidine and 4.3 g of benzylamine was heated at 115° C. for 20 hrs. under nitrogen gas. The crystals which formed on cooling were triturated with cyclohexane to remove excess benzylamine. Yield was 40 g (74%), m.p. 100°–125° C. The dimeleate salt made in i-PrOH melted at 180°–182° with decomposition.

Analysis: Calculated for $C_{25}H_{34}N_2O_9$: C,59.28; H,6.77; N,5.53. Found: C,59.29; H,6.72; N,5.50.

EXAMPLE 9

Trans-N-(1-cyclohexyl-4-hydroxy-3-pyrrolidinyl)-N-phenylmethyl-4-nitrobenzamide Hydrobromide.

A solution of 13.7 g (0.05 mole) of 4-benzylamino-1-cyclohexyl-3-pyrrolidinol in 300 ml of methylene chloride was cooled to 0° C. and 13 g of powdered anhydrous potassium carbonate was added. The mixture was stirred while a solution of 9.3 g (0.05 mole) of p-nitrobenzoyl chloride in 100 ml of methylene chloride was added dropwise. When the addition was complete, the mixture was allowed to warm to room temperature and stir for 18 hrs. The mixture was extracted with water, the methylene chloride was removed and the 21 g of residue was dissolved in ether and converted to the hydrobromide, filtered and dried; m.p. 230.0°–233.5° C.

Analysis: Calculated for $C_{24}H_{30}N_3O_4Br$: C,57.15; H,6.00; N,8.33. Found: C,57.29; H,6.08; N,8.17.

EXAMPLE 10

Trans-1-cyclohexyl-4-methylamino-3-pyrrolidinol Dimaleate.

A mixture of 83.5 g of 1-cyclohexyl-3,4-epoxypyrrolidine and 300 ml of liquid methyl amine was placed in a Parr bomb and rotated in a 120° C. oven for 17 hrs. The mixture was cooled and the excess methylamine was allowed to evaporate. The residue was crystallized by dissolving in benzene and then removing the solvent under vacuum. A small portion was converted to the dimaleate salt in isopropyl alcohol, washed with acetone and dried, m.p. 158°–159° C.

Analysis: Calculated for $C_{19}H_{30}N_2O_9$: C,53.02; H,7.03; N,6.51. Found: C,52.87; H,7.04; N,6.18.

EXAMPLE 11

Trans-N-(1-cyclohexyl-4-hydroxy-3-pyrrolidinyl)-N-methylbenzamide Hydrochloride.

A solution of trans-1-cyclohexyl-4-methylamino-3-pyrrolidinol (19.8 g) in 200 ml of methylene chloride was cooled to 5° C. and 20 g of powdered, anhydrous potassium carbonate was added. The mixture was stirred and cooled while 14.1 g of benzoyl chloride in 100 ml of methylene chloride was added dropwise. The mixture was allowed to come to room temperature and stirred for 24 hr., then heated at reflux for 5 hrs. The mixture was cooled and extracted with water. The methylene chloride was evaporated and the residue was converted to the hydrochloride and recrystallized twice from isopropyl alcohol, m.p. 184°–186.5° C.

Analysis: Calculated for $C_{18}H_{27}N_2O_2Cl$: C,63.80; H,8.03; N,8.27. Found: C,63.78; H,8.16; N,8.06.

EXAMPLE 12

Trans-N-(1-cyclohexyl-4-methoxypyrrolidin-3-yl)-N-methylbenzamide Fumarate.

A solution of 5.3 g (17.5 mmol) of the trans-N-(1-cyclohexyl-4-hydroxy-3-pyrrolidinyl)-N-methylbenzamide in 50 ml of dimethylformamide was added dropwise to 0.44 g (18.3 mmol) of sodium hydride (0.77 g of 57% sodium hydride in oil which had been washed with diethyl ether and dried). When hydrogen evolution was complete, the mixture was maintained below 15° C. while a solution of 2.5 g (17.6 mmol) of methyliodide in 20 ml of dimethylformamide was added dropwise. The mixture was stirred at ambient temperature for 4 hrs, diluted with 300 ml of water and extracted with methylene chloride. Chromatographing the 4.0 g. of crude product from the concentrated methylene chloride extracts gave 2.0 g (37%) of product. The fumarate, a white solid, m.p. 150.0°–151.5° C. was formed in isopropyl alcohol-diethyl ether.

Analysis: Calculated for $C_{23}H_{32}N_2O_6$: C,63.87; H,7.46; N,6.48. Found: C,63.77; H,7.47; N,6.42.

EXAMPLE 13

Trans-N-(1-cyclohexyl-4-hydroxy-3-pyrrolidinyl)-N-methyl-4-nitrobenzamide Fumarate.

A solution of 30 g (0.15 mole) of trans-1-cyclohexyl-4-methylamino-3-pyrrolidinol in 300 ml of methylene chloride was cooled to 5° C. and 30 g of powdered anhydrous potassium carbonate was added. This mixture was stirred and maintained below 10° C. while a solution of 28 g (0.15 mole) of p-nitrobenzoyl chloride in 200 ml of methylene chloride was added dropwise.

When addition was complete, the mixture was allowed to warm to room temperature and stirred for 18 hrs. After extraction with water and drying over anhydrous sodium sulfate, the organic layer was evaporated under vacuum. A small amount of the quantitative yield of residue was converted to the fumarate in isopropyl alcohol, m.p. 140.0°–144.5° C.

Analysis: Calculated for $C_{22}H_{29}N_3O_8$: C,57.01; H,6.31; N,9.07. Found: C,56.56; H,6.30; N,9.00.

EXAMPLE 14

Trans-4-amino-N-(1-cyclohexyl-4-hydroxy-3-pyrrolidinyl)-N-methylbenzamide.

A solution of 44 g of trans-N-(1-cyclohexyl-4-hydroxy-3-pyrrolidinyl)-N-methyl-4-nitrobenzamide in 600 ml of absolute ethanol was treated with a catalytic amount of platinum oxide and shaken in the Parr apparatus under hydrogen for one hour. The suspension was filtered and the filtrate evaporated under vacuum. The residue crystallized from a benzene-cyclohexane mixture and was recrystallized from toluene. The yield was 39.6 g (99%); m.p. 180.0°–182.5° C.

Analysis: Calculated for $C_{18}H_{27}N_3O_2$: C,68.11; H,8.57; N,13.24. Found: C,68.42; H,8.65; N,13.13.

EXAMPLE 15

Trans-4-acetylamino-N-(1-cyclohexyl-4-hydroxy-3-pyrrolidinyl)-N-methylbenzamide Hydrate.

A solution of 19 g. of trans-4-amino-N-(1-cyclohexyl-4-hydroxy-3-pyrrolidinyl)-N-methylbenzamide in 500 ml of p-dioxane was cooled to 10° and 30 g of powdered anhydrous potassium carbonate was added. The mixture was stirred and kept cool while 4.7 g of acetyl chloride in 50 ml of methylene chloride was added dropwise. The mixture was allowed to warm to room temperature and stirred for 24 hr. The mixture was filtered, the solvent was removed under vacuum and the residue was crystallized from aqueous acetone. Yield was 73%, m.p. 123°–127° C.

Analysis: Calculated for $C_{20}H_{31}N_3O_4$: C,63.64; H,8.29; N,11.13. Found: C,63.65; H,8.35; N,11.19.

EXAMPLE 16

Trans-N-(1-cyclohexyl-4-hydroxypyrrolidin-3-yl)-N-methyl-1-naphthalenecarboxamide Hydrochloride.

A solution of 10 g (0.05 mole) of trans-1-cyclohexyl-4-methylamino-3-pyrrolidinol in 100 ml of methylene chloride was mixed with 10 g of powdered anhydrous potassium carbonate and stirred while a solution of 10 g (0.05 mole) of 1-naphthoyl chloride in 50 ml of methylene chloride was added dropwise. The mixture was stirred for 2 hrs and then heated at reflux for 24 hrs. After cooling, the mixture was washed with water and the organic fraction was evaporated under vacuum. The residue was chromatographed on silica gel, eluting with acetone. Ten grams of the base, 56% yield, were collected and converted to the hydrochloride. After recrystallization from isopropyl alcohol, the salt melted at 238°–241° C.

Analysis: Calculated for $C_{22}H_{29}ClN_2O_2$: C,67.94; H,7.52; N,7.20. Found: C,67.97; H,7.53; N,7.16.

EXAMPLE 17

Trans-4-chloro-N-(1-cyclohexyl-4-hydroxy-3-pyrrolidinyl)-N-methylbenzamide Hydrochloride.

This compound was made according to the procedure of Example 11, using 10 g trans-1-cyclohexyl-4-methylamino-3-pyrrolidinol, 10 g of potassium carbonate and 8.9 g of p-chlorobenzoyl chloride in comparable quantities of solvent. The melting point of the salt was 215.0°–218° C.

Analysis: Calculated for $C_{18}H_{26}N_2O_2Cl_2$: C,57.91; H,7.02; N,7.50. Found: C,57.76; H,6.87; N,7.43.

EXAMPLE 18

Trans-1-ethyl-4-methylamino-3-pyrrolidinol Ethanedioate (2:3).

A bomb containing 27.2 g (0.24 mole) of 1-ethyl-3,4-epoxypyrrolidine was cooled to −20° and 50 ml of liquid (−30° C.) methylamine was added. The bomb was heated at 120° C. while rotating for 15 hr. The bomb and contents were then cooled and the mixture was put under nitrogen gas and diluted with ether. The mixture was stirred and allowed to come to room temperature. Removal of the solvent left 34.6 g (100%) of white crystalline residue. A small quantity of the residue was converted to the oxalate as a white powder; m.p. 175° (d)C.

Analysis: Calculated for $C_{10}H_{19}N_2O_7$: C,43.01; H,6.86; N,10.03. Found: C,42.95; H,6.85; N,9.74.

EXAMPLE 19

Trans-4-chloro-N-(1-ethyl-4-hydroxy-3-pyrrolidinyl)-N-methylbenzamide.

A solution of 17.0 g (118 mmoles) of trans-1-ethyl-4-methylamino-3-pyrrolidinol in 180 ml of methylene chloride was mixed with 15 g of powdered anhydrous potassium carbonate and cooled to −5° C. The mixture was kept at or below 0° C. while a solution of 20.6 g (118 mmoles) of p-chlorobenzoyl chloride in 100 ml of methylene chloride was added dropwise. After the mixture was stirred at ambient temperature for 18 hr, it was poured into 100 ml of water. The organic layer was separated, dried and concentrated. The residue was crystallized from cyclohexane to give 25 g (75%) of white crystals, m.p. 91°–93° C.

Analysis: Calculated for $C_{14}H_{19}ClN_2O_2$: C,59.47; H,6.77; N,9.91. Found: C,59.39; H,6.73; N,9.88.

EXAMPLE 20

Trans-N-(1-ethyl-4-hydroxy-3-pyrrolidinyl)-N-methylbenzamide Hydrochloride.

A solution of 14 g (49.5 mmoles) of trans-4-chloro-N-(1-ethyl-4-hydroxy-3-pyrrolidinyl)-N-methylbenzamide in 150 ml of absolute ethanol was treated with ca. 0.5 g of palladium-on-charcoal catalyst and was shaken with hydrogen at 60° C. in the Parr reduction apparatus for 3 hr. The mixture was cooled and filtered and the filtrate was concentrated. The residue crystallized when it was stirred with 3:1 diethyl ether-acetone. Separation of the precipitate gave 13.7 g (97%) of white powder; m.p. 160°–163° C.

Analysis: Calculated for $C_{14}H_{21}ClN_2O_2$: C,59.05; H,7.43; N,9.84. Found: C,58.77; H,7.49; N,9.71.

EXAMPLE 21

Trans-N-(1-ethyl-4-hydroxy-3-pyrrolidinyl)-N-methyl-4-nitrobenzamide.

A solution of 17.0 g. (118 mmoles) of trans-1-ethyl-4-methylamino-3-pyrrolidinol in 180 ml of methylene chloride was mixed with 15 g of powdered anhydrous potassium carbonate and cooled to −5°. The mixture was kept at or below 0° C. while a solution of 22.0 g (118 mmoles) of p-nitrobenzoyl chloride in 100 ml of methylene chloride was added dropwise. After the mixture was stirred at ambient temperature for 18 hr, it was poured into 100 ml of water. The organic layer was separated, dried, and concentrated. The residue was crystallized from benzene to give 30 g (87%) of white crytals; m.p. 104°–108° C.

Analysis: Calculated for $C_{14}H_{19}N_3O_4$: C,57.33; H,6.53; N,14.33. Found: C,57.60; H,6.52; N,14.15.

EXAMPLE 22

Trans-4-amino-N-(1-ethyl-4-hydroxy-3-pyrrolidinyl)-N-methylbenzamide.

A solution of 23 g (79 mmoles) of trans-N-(1-ethyl-4-hydroxy-3-pyrrolidinyl)-N-methyl-4-nitrobenzamide in 250 ml of absolute ethanol was treated with platinum oxide and shaken with hydrogen at ambient temperature in the Parr reduction apparatus for 3 hr. The mixture was filtered and the filtrate was concentrated to give 20.6 g (100%) of crude product. One-half of the residue was crystallized from acetone to give 8.5 g (82%) of white powder; m.p. 142°–145° C.

Analysis: Calculated for $C_{14}H_{21}N_3O_2$: C,63.86; H,8.04; N,15.96. Found: C,65.56; H,8.10; N,15.79.

EXAMPLE 23

Trans-1-ethyl-4-[(diphenylmethyl)amino]-3-pyrrolidinol Di-(Z)-butenedioate.

A mixture of 11.3 g (0.1 mole) of 1-ethyl-3,4-epoxypyrrolidine, 18.3 g (0.1 mole) of diphenylmethylamine and two drops concentrated hydrochloric acid was heated at 145° C. overnight. The residue was triturated with cyclohexane and a solid precipitated. The solid was collected by filtration and recrystallized from cyclohexane to give 7.0 g (24%) of base as a white solid. This solid was converted to the dimaleate to yield a white solid, m.p. 132°–135° C. recrytstallized from isopropyl alcohol.

Analysis: Calculated for $C_{27}H_{32}N_2O_9$: C,61.36; H,6.10; N,5.30. Found: C,61.24; H,6.05; N,5.35.

EXAMPLE 24

Trans-1-ethyl-4-[(2-phenylethyl)amino]-3-pyrrolidinol Di-(Z)-Butenedioate.

A mixture of 11.3 g (0.1 mole) of N-ethyl-3,4-epoxypyrrolidine, 12.1 g (0.1 mole) of phenethylamine and one drop concentrated hydrochloric acid was heated at 120° C. under a nitrogen atmosphere overnight. The mixture solidified when cooled and the solid was washed with petroleum ether and collected by filtration. The solid was recrystallized from cyclohexane to give 15.0 g (64%) of the base as a white powder, m.p. 81°–83° C. A portion was converted to the dimaleate to yield whilte solid, m.p. 143°–145° C. recrystallized from absolute ethanol.

Analysis: Calculated for $C_{22}H_{30}N_2O_9$: C,56.65; H,6.48; N,6.01. Found: C,56.24; H,6.46; N,5.90.

EXAMPLE 25

Trans-N-(1-ethyl-4-hydroxy-3-pyrrolidinyl)-N-(2-phenylethyl)benzamide.

To a stirring slurry of 3.5 g (0.15 mole) of trans-1-ethyl-4-[(2-phenylethyl)amino]-3-pyrrolidinol and 5 g potassium carbonate in 75 ml of methylene chloride at ice bath temperature was added dropwise a solution of 3.2 g (0.023 mole) of benzoyl chloride in 25 ml of methylene chloride. After addition was complete, the mixture was stirred at ambient temperature overnight. The mixture was filtered through Celite and the filtrate was concentrated to give a yellow gum as residue. An NMR analysis of this gum indicated that it was a mixture of desired amide and the di-substituted amide-ester. The gum was dissolved in 50 ml ethanol and a solution of 0.5 g (0.08 mole) potassium hydroxide in 10 ml of water was added. The mixture was heated at reflux for 3 hr. The solution was concentrated and water was added to the residue. The mixture was extracted with methylene chloride and the combined extracts were dried over anhydrous sodium sulfate and concentrated to give 4.9 g (98%) of gum as residue. The gum crystallized upon standing and the solid was recrystallized from cyclohexane to yield white solid, m.p. 71°–75° C.

Analysis: Calculated for $C_{21}H_{26}N_2O_2$: C,74.53; H,7.74; N,8.28. Found: C,74.36; H,7.82; N,8.12.

EXAMPLE 26

Trans-1-ethyl-4-phenylamino-3-pyrrolidinol Dihydrochloride.

A mixture of 56.5 g (0.5 mole) of N-ethyl-3,4-epoxypyrrolidine, 46.5 g (0.5 mole) of aniline and 3 drops of concentrated hydrochloric acid was heated at 150° C. under a nitrogen atmosphere overnight. The reaction mixture was subjected to vacuum distillation at 110°/0.5 mm. to remove impurities and starting materials. The pot residue (60 g) was chromatographed on 1.2 kg of silica gel. The fraction eluted with 10% methanol in acetone amounted to 41.5 g (40%) and was determined to be the desired product. A portion of this oil was converted to the dihydrochloride, and the salt was recrystallized from isopropyl alcohol-diethyl ether to yield a pink solid; m.p. 158°–180° C.

Analysis: Calculated for $C_{12}H_{20}Cl_2N_2O$: C,51.62; H,7.22; N,10.03. Found: C,51.35; H,7.15; N,9.88.

EXAMPLE 27

Trans-4-chlorobenzoic Acid Ester with 4-[(4-Chlorobenzoyl)(phenyl)amino]-1-ethyl-3-pyrrolidinol (E)-2-butenedioate (3:4).

A mixture of12.5 g (0.058 mole) of crude trans-1-ethyl-4-phenylamino-3-pyrrolidinol, 350 ml methylene chloride, 100 ml acetone and 20 g of potassium carbonate was treated with a solution of 21 g (0.12 mole) of p-chlorobenzoylchloride in 150 ml of methylene chloride. The mixture was stirred at ambient temperature overnight and then 50 ml of water was added and the mixture stirred for 2 hr. The layers were separated and the methylene chloride layer was dried over anhydrous sodium sulfate and concentrated to give an oil as residue. The oil was triturated with cyclohexane and the mixture was filtered through Celite. The filtrate was treated with charcoal and concentrated to give 26.7 g (95%) of light brown gum as residue. A portion of this gum was converted to the fumarate and this salt was recrystallized from isopropanol to yield an off-white powder; m.p. 171°–172° C.

Analysis: Calculated for $C_{29}H_{27}Cl_2N_2O_6$: C,61.06; H,4.77; N,4.91. Found: C,60.89; H,4.84; N,4.86.

EXAMPLE 28

Trans-4-chloro-N-(1-ethyl-4-hydroxy-3-pyrrolindinyl)-N-phenylbenzamide Fumarate.

A mixture of 21.1 g (0.0437 mole) of trans-4-chlorobenzoic ester with 4-[(4-chlorobenzoyl)(phenyl)amino]-1-ethyl-3-pyrrolidinol, 2.6 g. (0.046 mole) of potassium hydroxide, 50 ml. of water and 200 ml. of methanol was heated at reflux for one hour. The solution was concentrated and the residue was poured into water. The mixture was extracted three times with methylene chloride and the combined extracts were washed with water, dried over anhydrous sodium sulfate and concentrated to 14.6 g of an oil as residue. The oil was converted to the fumarate and the salt was recrystallized from ethanol to yield 16.6 g (81%) of tan powder; m.p. 193°–195° d.C.

Analysis: Calculated for $C_{23}H_{25}ClN_2O_6$: C,59.94; H,5.67; N,6.08. Found: C,60.24; H,5.53; N,6.04.

EXAMPLE 29

Trans-N-(1-ethyl-4-hyroxy-3-pyrrolidinyl)-N-phenyl-benzamide (E)-2-butenedioate.

A solution of 6.4 g (0.0186 mole) of trans-4-chloro-N-(1-ethyl-4-hyroxy-3-pyrrolidinyl)-N-phenylbenzamide base in 75 ml of ethanol was hydrogenated over 10% palladium-on-charcoal at 60° overnight. The mixture was filtered through Celite and the filtrate was concentrated. The residue was partitioned between 10% sodium hydroxide and methylene chloride. The methylene chloride layer was dried over anhydrous sodium sulfate and concentrated to give 5.6 g. (97%) of oil as residue. The oil was converted to the fumarate and the salt was recrystallized from 95% ethanol to yield an off-white powder; m.p. 191°–193° C.

Analysis: Calculated for $C_{23}H_{26}N_2O_6$: C,64.78; H,6.15; N,6.57. Found: C,64.69; H,6.19; N,6.49.

EXAMPLE 30

Trans-1-ethyl-4-({2-[3,4-bis(phenylmethoxy)-phenyl]ethyl}amino)-3-pyrrolidinol Di-(Z)-Butenedioate.

A 10 g (0.027 mole) portion of 3,4-dibenzyloxyphenthylamine hydrochloride (Aldrich) was partitioned between methylene chloride and 50% sodium hydroxide. The methylene chloride layer was dried over anhydrous sodium sulfate and concentrated. To the residue was added 3.1 g (0.027 mole) of N-ethyl-3,4-epoxypyrrolidine and 2 drops concentrated hydrochloric acid. The reaction mixture was heated at 160° C. overnight. A portion of this reaction mixture was converted to the dimaleate to give a 93% yield of gray solid; m.p. 159°–161° C. (recrystallized from absolute ethanol).

Analysis: Calculated for $C_{36}H_{42}N_2O_{11}$: C,63.71; H,6.24; N,4.13. Found: C,63.54; H,6.14; N,4.02.

EXAMPLE 31

Trans-1-ethyl-4-[(10,11-dihydro-5H-dibenzo[a,d]cyclohepten-5-yl)amino]-3-pyrrolidinol (Z)-Butenedioate (9:4).

A mixture of 7.5 g (0.036 mole) of 5-amino-10,11-dihydro-5H-dibenzo[a,d]cycloheptene, 4.1 g (0.036 mole) of n-ethyl-3,4-epoxypyrrolidine and 2 drops concentrated hydrochloric acid was heated at 140° C. under a nitrogen atmosphere overnight. The residue was converted to the maleate. The salt was recrystallized twice from isopropyl alcohol, converted to the base, reconverted to the maleate, and recrystallized from isopropyl alcohol to yield 1.4 g. (7%) of white solid, m.p. 132°–135° C.

Analysis: Calculated for $C_{30}H_{35}N_2O_{10}$: C,61.74; H,6.05; N,4.80. Found: C,61.76; H,6.32; N,5.05.

EXAMPLE 32

2-(4-Chlorophenyl)-5-cyclohexyl-5,6-dihydro-4H-pyrrolo[3,4-d]oxazole Hydrochloride.

Two grams of trans-4-chloro-N-(1-cyclohexyl-4-hydroxy-3-pyrrolidinyl)benzamide was dissolved in 50 ml of cold (0° C.) sulfonyl chloride; the solution was allowed to warm to room temperature and stirred overnight. Excess sulfonyl chloride was removed at 50° C./60 mm. Fifty milliliters of carbon tetrachloride was added to the residue and then evaporated under vacuum. When acetone was added to the residue, it crystallized to a white solid (quantitative yield). Recrystallization from absolute ethanol gave product, m.p. 303°–304° C.

Analysis: Calculated for $C_{17}H_{22}N_2OCl_2$: C,59.83; H,6.50; N,8.21. Found: C,59.58; H,6.56; N,8.12.

EXAMPLE 33

Cis-4-chloro-N-(1-cyclohexyl-4-hydroxy-3-pyrrolidinyl)benzamide.

Forty-one grams of 2-(4-chlorophenyl)-5-cyclohexyl-5,6-dihydro-4H-pyrrolo-[3,4-d]oxazole was dissolved in 500 ml. of 95% ethanol and the solution was heated at reflux for one hour. The solvent was evaporated under vacuum and replaced with methylene chloride. The methyl chloride was washed with dilute sodium hydroxide, dried and evaporated. The product was crystallized from benzene. Yield was 33.2 g (94.5%); m.p. 158°–160° C.

Analysis: Calculated for $C_{17}H_{23}N_2O_2Cl$: C,63.25; H,7.18; N,8.68. Found: C,63.15; H,7.24; N,8.67.

EXAMPLE 34

Cis-N-(1-cyclohexyl-4-hydroxy-1-pyrrolidinyl)benzamide.

A solution of 6.5 g (0.02 mole) of cis-4-chloro-N-(1-cyclohexyl-4-hydroxy-3-pyrrolidinyl)benzamide in 150 ml of absolute ethanol was treated with ca. 0.5 g of 10% palladium-on-charcoal catalyst and was shaken with hydrogen at 60° C. in the Parr reduction apparatus for 2 hr. After cooling, the suspension was filtered and the solvent was evaporated under aspirator vacuum. The residue was dissolved in methylene chloride, washed with dilute sodium hydroxide solution, then water; the organic layer was dried over anydrous sodium sulfate and the solvent was evaporated. The yield of crystalline residue melting at 127.0°–30.5° C. was 5.45 g (95%). The product was recrystallized from benzene; m.p. 127.5°–129.0° C.

Analysis: Calculated for $C_{17}H_{24}N_2O_2$: C,70.80; H,8.39; L N,9.71. Found: C,70.53; H,8.45; N,9.65.

EXAMPLE 35

Cis-1-cyclohexyl-4-[(phenylmethyl)amino]-3-pyrrolidinol.

A mixture of 19 g (0.06 mole) of cis-N-(1-cyclohexyl-4-hydroxy-1-pyrrolidinyl)benzamide was added to a solution of 37 g (0.13 mole) of 70% Red-Al in 500 ml of dry benzene and heated at reflux for 18 hr. The solution was then cooled and decomposed with 125 ml of 20% sodium hydroxide. The benzene layer was separated, washed twice with water, dried over anhydrous sodium sulfate and evaporated to dryness. The white solid remaining melted at 108.5°–110.0° C. and weighed 18 g (99%). A small quantity was recrystallized from benzene and the melting point remained constant.

Analysis: Calculated for $C_{17}H_{26}N_2O$: C,74.41; H,9.55; N,10.21. Found: C,74.13; H,9.56; N,10.17.

EXAMPLE 36

Cis-3-amino-1-cyclohexyl-4-pyrrolindol.

A solution of 17.5 g (0.064 mole) of cis-1-cyclohexyl-4-[(phenylmethyl)amino]-3-pyrrolidinol in 600 ml of ethanol was mixed with 0.5 g of 10% palladium-on-charcoal catalyst and hydrogenated with hydrogen at 60° C. for 4 hrs. The suspension was then cooled and filtered and the filtrate concentrated to yield 11.6 g. (99%) of the titled compound.

EXAMPLE 37

Cis-N-(1-cyclohexyl-4-hydroxy-1-pyrrolidinyl)-4-nitrobenzamide.

A solution of 10.5 g (0.057 mole) of cis-3amino-1-cyclohexyl-4-pyrrolidinol in 300 ml of methylene chloride was cooled to 5° C. and stirred with 10 g of powdered potassium carbonate while adding dropwise a solution of 10.6 g (0.057 mole) of p-nitrobenzoyl chloride in 100 ml of methylene chloride. After the addition was complete, the mixture was allowed to warm to room temperature and thereafter stirred for 18 hrs. The slurry was extracted with water and the remaining methylene chloride solution was dried over anhydrous sodium sulfate and evaporated to remove the methylene chloride. The yellow residue crystallized and was recrystallized from acetone. Resulting yellow needles weighed 15.6 g (82%), m.p. 135.5°–138° C.

Analysis: Calculated for $C_{17}H_{23}N_3O_4$: C,61.25; H,6.95; N,12.60. Found: C,61.07; H,6.98; N,12.56.

EXAMPLE 38

Cis-4-amino-N-(1-cyclohexyl-4-hydroxy-3-pyrrolidinyl)benzamide.

A solution of 12.3 g (0.037 mole) of cis-N-(1-cyclohexyl-4-hydroxy-1-pyrrolidinyl)-4-nitrobenzamide in 500 ml of ethanol was treated with a catalytic amount of platinum oxide and shaken in a Parr reduction apparatus under hydrogen for one hour. The mixture was then filtered and the solvent was evaporated. The residue was crystallized from acetone. The yield of white solid melting at 176.0°–177.5° C. was 10.8 g (96.5%).

Analysis: Calculated for $C_{17}H_{25}N_3O_2$: C,67.30; H,8.31; N,13.85. Found: C,67.05; H,8.35; N,13.76.

EXAMPLE 39

Cis-4-acetylamino-N-(1-cyclohexyl-4-hydroxy-3-pyrrolidinyl)benzamide.

A solution of 6.0 g (0.02 mole) of cis-4-amino-N-(1-cyclohexyl-4-hydroxy-3-pyrrolidinyl)benzamide in 250 ml of tetrahydrofuran was mixed with 8 g of powdered anhydrous potassium carbonate and stirred while 1.6 g (0.02 mole) of acetyl chloride was added dropwise. The mixture was stirred for 18 hr. The tetrahydrofuran was removed and the residue was partitioned between water and chloroform. The chloroform was separated and in a short time the product precipitated. The precipitate was filtered and then triturated with boiling acetone, filtered and dried. The yield of product melting at 200.0°–203.0° C. was 5.1 g (74%).

Analysis: Calculated for $C_{19}H_{27}N_3O_3$: C,66.06; H,7.88; N,12.16. Found: C,65.66; H,7.90; N,12.06.

EXAMPLE 40

Trans-4-amino-1-benzyl-3-pyrrolidinol Maleate.

Utilizing the procedure of Example 1 but substituting an equal molar amount of 1-benzyl-3,4-epoxypyrrolidine for 1-cyclohexyl-3,4-epoxypyrrolidine, the titled compound is obtained.

EXAMPLE 41

Trans-4-aminomethyl-1-benzyl-3-pyrrolidinol Maleate.

By utilizing the procedure of Example 10 but substituting trans-1-benzyl-3,4-epoxypyrrolidine for 1-cyclohexyl-3,4-epoxypyrrolidine, the title compound is obtained.

EXAMPLE 42

Trans-N-(1-benzyl-4-hydroxy-3-pyrrolidinyl)benzamide.

By utilizing the procedure of Example 3 but substituting trans-4-amino-1-benzyl-3pyrrolidine for trans-4-amino-1-cyclohexylpyrrolidine, the title compound is obtained.

EXAMPLE 43

Trans-N-(4-hydroxy-3-pyrrolidinyl)benzamide

A mixture of trans-N-(1-benzyl-4-hydroxy-3-pyrrolidinyl)benzamide and palladium-on-charcoal catalyst is hydrogenated at 60° C. for 4 hrs. to obtain the title compound.

EXAMPLE 44

Trans-4-n-butylamino-1-ethyl-3-pyrrolidinol.

A mixture of 22.6 g (0.20 mole) of 3,4-epoxy-1-ethylpyrrolidine, 29.2 g (0.40 mol) of n-butylamine and one drop of conc. hydrochloric acid was heated in a bomb at 150° C. for 20 hr. The mixture was cooled to room temperature, diluted with 350 ml of petroleum ether, cooled in an ice bath and the precipitate was collected. The yield of pure compound as white flakes in this step was 18.0 g (48%); m.p. 57.5°–59.0° C. The filtrate was concentrated under high vaccum leaving a residue of 17.5 g (47%) of quite pure product. Total yield in the two steps was 35.5 g (about 95%).

Analysis: Calculated for $C_{10}H_{22}N_2O$: C,64.47; H,11.90; N,15.04. Found: C,64.24; H,11.94; N,15.09.

EXAMPLE 45

Trans-4-cyclohexylamino-1-ethyl-3-pyrrolidinol.

A mixture of 11.3 g (0.10 mole) of 3,4-epoxy-1-ethylpyrrolidine, 11.9 g (0.12 mol) of cyclohexylamine and one drop of conc. hydrochloric acid was heated at 130° C. under a nitrogen atmosphere for 18 hr. The mixture was cooled and diluted with 200 ml of petroleum ether. The precipitate was collected and recrystallized from petroleum-ether-cyclohexane to give 15 g (71%) of a white powder; m.p. 68°–71° C.

Analysis: Calculated for $C_{12}H_{24}N_2O$: C,67.88; H,11.39; N,13.19. Found: C,67.46; H,11.41; N,13.18.

EXAMPLE 46

Trans-4-chlorobenzoic Acid Ester with 4-[(4-chlorobenzoyl)(n-butyl)amino]-1-ethyl-3-pyrrolidinol.

A mixture of 17 g (0.091 mole) of trans-4-n-butylamine-1-ethyl-3-pyrrolidinol, 20 g of anhydrous potassium carbonate and 150 ml of methylene chloride was treated dropwise with 35 g (0.20 mole) of p-chlorobenzoyl chloride. The mixture was stirred for 18 hr, then washed with water, dried over magnesium sulfate and concentrated under reduced pressure. The brown syrup was dissolved in hot isopropyl ether, filtered to remove insoluble impurities and then the filtrate cooled. The deposited crystals were collected and dried to give 31 g (73%) of white needles, m.p. 104°-106° C.

Analysis: Calculated for $C_{24}H_{28}N_2O_3Cl_2$: C,62.21; H,6.09; N,6.05. Found: C,62.22; H,6.09; N,6.05.

EXAMPLE 47

Trans-4-chlorobenzoic Acid Ester with 4-[(4-chlorobenzoyl)(cyclohexyl)amino]-1-ethyl-3-pyrrolidinol Fumarate [1:1].

To a mixture of 3.0 g (0.014 mole) of trans-4-cyclohexylamino-1-ethyl-3-pyrrolidinol and 3.0 g of anhydrous potassium carbonate in 80 ml of methylene chloride was added dropwise 5.2 g (0.03 mole) of p-chlorobenzoyl chloride. The mixture was stirred for 18 hr, then washed with water, dried over magnesium sulfate and concentrated under reduced pressure. The yield of crude product as a brown syrup was 6.9 g (about 100%). A small portion of the syrup was dissolved in isopropyl alcohol and treated with fumaric acid to give white crystals; m.p. 147°-150° C.

Analysis: Calculated for $C_{30}H_{34}N_2O_7Cl_2$: C,59.51; H,5.66; N,4.63. Found: C,59.48; H,5.76; N,4.57.

EXAMPLE 48

Trans-benzoic Acid Ester with 4-[(benzoyl)(cyclohexyl)amino]-1-ethyl-3-pyrrolidinol Fumarate [1:1].

To a mixture of 4.9 g (0.023 mole) of trans-4-cyclohexylamino-1-ethyl-3-pyrrolidinol and 5.0 g of anhydrous potassium carbonate in 50 ml of methylene chloride was added dropwise 7.0 g (0.05 mole) of benzoyl chloride. The mixture was stirred for 18 hr, then washed with water, dried over magnesium sulfate and concentrated under reduced pressure. The yield of crude product as a brown syrup was 7.8 g (about 81%). A 7.2 g portion of the syrup was treated with 2.0 g of fumaric acid in 60 ml of ethyl acetate. The mixture was heated on a steam bath until solution was complete, then cooled and the precipitate collected and dried to give 6.8 g of white powder; m.p. 162.5°-164.5° C.

Analysis: Calculated for $C_{30}H_{36}N_2O_7$: C,67.15; H,6.76; N,5.22. Found: C,67.01; H,6.73; N,5.13.

EXAMPLE 49

Trans-4-[(4-chlorobenzoyl)(n-butyl)amino]-1-ethyl-3-pyrrolidinol.

A mixture of 7.0 g (0.015 mole) of trans-4-chlorobenzoic acid ester with 4-[(4-chlorobenzoyl)(n-butyl)amino]1-ethyl-3-pyrrolidinol, 0.9 g (0.016 mole) of potassium hydroxide, 15 ml of water and 60 ml of methanol was heated on a steam bath for 1 hr, then concentrated to approximately 10 ml volume under reduced pressure. The residue was partitioned between water and methylene chloride. The organic layer was separated, dried and concentrated under reduced pressure. The crystalline residue was recrystallized from isopropyl ether to give 4.3 g (89%) of white powder; m.p. 96.5°-98.0° C.

Analysis: Calculated for $C_{17}H_{25}N_2O_2Cl$: C,62.86; H,7.76; N,8.62. Found: C,62.78; H,7.80; N,8.58.

EXAMPLE 50

Trans-4-[(benzoyl)(cyclohexyl)amino]-1-ethyl-3-pyrrolidinol Fumarate [1:1].

A mixture of 4.8 g (9 mmole) of trans-benzoic acid ester with 4-[(benzoyl)(cyclohexyl)amino]-1-ethyl-3-pyrrolidinol fumarate [1:1], 1.7 g (30 mmole) of potassium hydroxide, 10 ml of water and 40 ml of methanol was heated on a steam bath for 1 hr. then concentrated to approximately 5-10 ml volume under reduced pressure. The residue was partitioned between water and methylene chloride and the organic layer was dried and concentrated under reduced pressure. The residue was dissolved in ethyl acetate and 1.0 g fumaric acid added and the precipitate was collected. After recrystallization from ethyl acetate, 2.7 g (72%) of white powder, m.p. 145.0°-146.5° C. was obtained.

Analysis: Calculated for $C_{23}H_{32}N_2O_6$: C,63.87 H,7.46; N,6.48. Found: C,63.50; H,7.48; N,6.39.

EXAMPLE 51

Trans-4-[(4-chlorobenzoyl)(cyclohexyl)amino]-1-ethyl-3-pyrrolidinol.

A mixture of 6.9 g (0.014 mole) of trans-4-chlorobenzoic acid ester with 4-[(4-chlorobenzoyl)(cyclohexyl)amino]-1-ethyl-3-pyrrolidinol, 0.9 g (0.016 mole) of potassium hydroxide, 10 ml of water and 40 ml of methanol was heated on a steam bath for 1 hr. then concentrated to 10 ml volume under reduced pressure. The residue was partitioned between water and methylene chloride and the organic layer was dried and conentrated under reduced pressure. After recrystallization from 60% aqueous methanol, 3.5 g (72%) of white powder, m.p. 111°-116° C. was obtained.

Analysis: Calculated for $C_{19}H_{27}N_2O_2Cl$: C,65.04; H,7.76; N,7.98. Found: C,64.73; H,7.88; N,7.91.

EXAMPLE 52

Trans-benzoic Acid Ester with 4-[(benzoyl)(n-butyl)amino]-1-ethyl-3-pyrrolidinol.

A solution of 4.6 g (0.01 mol) of trans-4-chloro-benzoic acid ester with 4-[(4-chlorobenzoyl)(n-butyl)amino]1-ethyl-3-pyrrolidinol in 100 ml of 190 ethanol was treated with 1.6 g (0.02 mol) of 50% aqueous sodium hydroxide and 0.5 g of 10% palladium-on-charcoal catalyst, and hydrogenated at 45 lb hydrogen pressure and 60° C. for 3 hr. The mixture was cooled and filtered to remove impurities and the filtrate was concentrated under reduced pressure. The crystalline residue was recrystallized from isopropyl ether to give 2.5 g (64%) of white powder, m.p. 106°-108° C.

Analysis: Calculated for $C_{24}H_{30}N_2O_3$: C,73.07; H,7.67; N,7.10. Found: C,72.88; H,7.64; N,7.03.

EXAMPLE 53

Trans-4-[(benzoyl)(n-butyl)amino]-1-ethyl-3-pyrrolidinol Fumarate [1:1].

A combination of 4.3 g (0.013 mole) of trans-4-[(4-chlorobenzoyl)(n-butyl)amino]-1-ethyl-3-pyrrolidinol, 0.8 g (0.14 mole) of potassium hydroxide in 10 ml of water and 50 ml of tetrahydrofuran was hydrogenated at 45 lb hydrogen pressure and 60° C. for 3 hr. The mixture was cooled and filtered to remove impurities and the filtrate was concentrated under reduced pressure. The residue was reacted with fumaric acid in ethyl acetate and recrystallized from ethyl acetate to give 1.6 g (20%) as white powder, m.p. 106°–108° C.

Analysis: Calculated for $C_{21}H_{30}N_2O_6$: C,62.05; H,7.44; N,6.89. Found: C,61.68; H,7.40; N,6.85.

Formulation and Administration

Effective quantities of any of the foregoing pharmacologically active compounds of Formula I may be administered to a living animal body for therapeutic purposes according to usual modes of administration and in usual forms such as orally in solutions, emulsions, suspensions, pills, tablets and capsules in pharmaceutically acceptable carriers and parenterally in the form of sterile solutions.

For the parenteral administration, the carrier or excipient may be a sterile, parenterally acceptable liquid, e.g., water or a parenterally acceptable oil, e.g., arachis oil contained in an ampoule.

Although very small quantities of the active materials of the present invention are effective when minor therapy is involved or in cases of administration to subjects having a relatively low body weight or adolescents and the elderly, unit dosages are usually from five milligrams or above and preferably 25, 50 or 100 milligrams or even higher, depending of course upon the emergency of the situation and the particular amount of alleviation of depression sought in treatment of the host. Five to 50 milligrams appears optimum per unit dose. Broader ranges appear to be 1 to 500 milligrams per unit dose depending on all of the above and the strength of antidepressant activity of the individual compounds and the reaction of the host to the agent. Daily oral dosages for a 70 kg host should preferably range from about 10 mg to about 150 mg in one dose at night or several dosage units administered at intervals, and daily intramuscular dosages for a 70 kg host should also preferably range from about 10 to about 150 mg broken into about 2 to 4 individual doses per day at the higher dosage levels. More especially, for a living animal generally, daily oral dosages of the more active compounds of Examples 27, 28 and 29 will preferably range from about 0.2 to 2 mg/kg body weight.

The following formulations are representative for all of the pharmacologically active compounds of this invention.

1. Capsules

Capsules of 5 mg., 10 mg., 25 mg., and 50 mg. of active ingredient per capsule are prepared. With the higher amounts of active ingredient, reduction may be made in the amount of lactose.

| Typical blend for encapsulation | Per Capsule, mg. |
| --- | --- |
| Active ingredient | 5 |
| Lactose | 259 |
| Starch | 126 |
| Magnesium stearate | 4 |
| | 394 |

Uniformly blend the selected active ingredient with lactose, starch and magnesium stearate and encapsulate the blend in gelatin capsules.

2. Tablets

A typical formulation for a tablet containing 5.0 mg of active ingredient per table follows. The formulation may be used for other strengths of active ingredients by adjustment of weight of dicalcium phosphate.

| | Per Tablet, mg. |
| --- | --- |
| (1) Active ingredient | 5.0 |
| (2) Corn starch | 15.0 |
| (3) Corn starch (paste) | 12.0 |
| (4) Lactose | 35.0 |
| (5) Dicalcium phosphate | 132.0 |
| (6) Calcium stearate | 2.0 |
| | 201.0 |

Uniformly blend (1), (2), (4) and (5). Prepare (3) as a 10 percent paste in water. Granulate the blend with starch paste and pass the wet mass through an 8 mesh screen. The wet granulation is dried and sized through a 12 mesh screen. The dried granules are blended with the calcium stearate and compressed.

3. Injectable Sterile Solution

| | Per cc |
| --- | --- |
| Active ingredient, e.g. Ex. 28 | 10 mg. |
| Preservative, e.g. chlorobutanol, wt/vol % | 20 mg. |
| Dextrose | 44 mg. |
| Water qs to 1 ml | 1 ml |

Prepare solution, clarify by filtration, fill into vials, seal and autoclave.

Various modifications and equivalents will be apparent to one skilled in the art and may be made in the compounds, compositions and methods of the present invention without departing from the spirit or scope thereof, and it is therefore understood that the invention is to be limited only by the scope of the appended claims.

What is claimed is:

1. A compound selected from 3-amino-4-hydroxypyrrolidines having the formula:

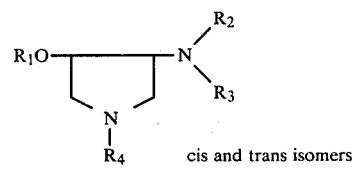

cis and trans isomers wherein;

$R_1$ is hydrogen, loweralkyl or phenylcarbonyl,

R$_2$ is hydrogen, loweralkyl, lowercycloalkyl, phenyl, or phenylloweralkyl,

R$_3$ is hydrogen, loweralkyl, phenylloweralkyl, phenylcarbonyl, diphenylmethyl, -5-yl-10,11-dihydro-5H dibenzo[a,d]cycloheptene, or naphthyl-carbonyl, R$_4$ is hydrogen, loweralkyl, phenylloweralkyl or lowercycloalkyl, Phenyl is unsubstituted phenyl or phenyl substituted by 1 to 3 groups selected from halogen, alkyl, loweralkoxy, trifluoromethyl, benzyloxy, nitro, amino, acetamido, and hydroxy, and the pharmaceutically acceptable acid addition salts thereof.

2. A compound of claim 1 which is trans-4-chlorobenzoic acid ester with 4-[(4-chlorobenzoyl)(phenyl)amino]-1-ethyl-3-pyrrolidinol.

3. A compound of claim 1 which is trans-4-chlorobenzoic acid ester with 4-[(4-chlorobenzoyl)(phenyl)amino]-1-ethyl-3-pyrrolidinol fumarate.

4. A compound of claim 1 which is trans-4-chloro-N-(1-ethyl-4-hydroxy-3-pyrrolidinyl)-N-phenylbenzamide.

5. A compound of claim 1 which is trans-4-chloro-N-(1-ethyl-4-hydroxy-3-pyrrolidinyl)-N-phenylbenzamide fumarate.

6. A compound of claim 1 which is trans-N-(1-ethyl-4-hydroxy-3-pyrrolidinyl)-N-phenylbenzamide.

7. A compound of claim 1 which is trans-N-(1-ethyl-4-hydroxy-3-pyrrolidinyl)-N-phenylbenzamide fumarate.

8. A compound of claim 1 which is trans-4-amino-1-cyclohexyl-3-pyrrolidinol.

9. A compound of claim 1 which is trans-4-amino-1-cyclohexyl-3-pyrrolidinol dimaleate.

10. A compound of claim 1 which is trans-4-chloro-N-(1-cyclohexyl-4-hydroxy-3-pyrrolidinyl)benzamide.

11. A compound of claim 1 which is trans-N-(1-cyclohexyl-4-hydroxy-3-pyrrolidinyl)benzamide.

12. A compound of claim 1 which is trans-4-acetylamino-N-(1-cyclohexyl-4-hydroxy-3-pyrrolidinyl)benzamide.

13. A compound of claim 1 which is trans-4-acetylamino-N-(1-cyclohexyl-4-hydroxy-3-pyrrolidinyl)benzamide hydrate (1:4).

14. A compound of claim 1 which is trans-N-(cyclohexyl-4-hydroxy-3-pyrrolidinyl)-4-nitrobenzamide.

15. A compound of claim 1 which is trans-4-nitrobenzoic acid ester with 1-cyclohexyl-3-{[(4-nitrophenyl)carbonyl]amino}-3-pyrrolidinol.

16. A compound of claim 1 which is trans-4-amino-N-(1-cyclohexyl-4-hydroxy-pyrrolidine-3-yl)benzamide.

17. A compound of claim 1 which is trans-1-cyclohexyl-4-phenylmethylamino-3-pyrrolidinol.

18. A compound of claim 1 which is trans-1-cyclohexyl-4-phenylmethylamino-3-pyrrolidinol dimaleate.

19. A compound of claim 1 which is trans-N-(1-cyclohexyl-4-hydroxy-3-pyrrolidinyl)-N-phenylmethyl-4-nitrobenzamide.

20. A compound of claim 1 which is trans-N-(1-cyclohexyl-4-hydroxy-3-pyrrolidinyl)-N-phenylmethyl-4-nitrobenzamide hydrobromide.

21. A compound of claim 1 which is trans-1-cyclohexyl-4-methylamino-3-pyrrolidinol.

22. A compound of claim 1 which is trans-1-cyclohexyl-4-methylamino-3-pyrrolidinol dimaleate.

23. A compound of claim 1 which is trans-N-(cyclohexyl-4-hydroxy-3-pyrrolidinyl)-N-methylbenzamide.

24. A compound of claim 1 which is trans-N-(cyclohexyl-4-hydroxy-3-pyrrolidinyl)-N-methylbenzamide hydrochloride.

25. A compound of claim 1 which is trans-N-(1-cyclohexyl-4-methoxypyrrolidine-3-yl)-N-methylbenzamide.

26. A compound of claim 1 which is trans-N-(1-cyclohexyl-4-methoxypyrrolidin-3-yl)-N-methylbenzamide fumarate.

27. A compound of claim 1 which is trans-N-(1-cyclohexyl-4-hydroxy-3-pyrrolidinyl)-N-methyl-4-nitrobenzamide.

28. A compound of claim 1 which is trans-N-(cyclohexyl-4-hydroxy-3-pyrrolidinyl)-N-methyl-4-nitrobenzamide fumarate.

29. A compound of claim 1 which is trans-4-amino-N-(1-cyclohexyl-4-hydroxy-3-pyrrolidinyl)-N-methylbenzamide.

30. A compound of claim 1 which is trans-4-acetylamino-N-(1-cyclohexyl-4-hydroxy-3-pyrrolidinyl)-N-methylbenzamide.

31. A compound of claim 1 which is trans-4-acetylamino-N-(1-cyclohexyl-4-hydroxy-3-pyrrolidinyl)-N-methylbenzamide hydrate.

32. A compound of claim 1 which is trans-N-(1-cyclohexyl-4-hydroxypyrrolidin-3-yl)-N-methyl-1-naphthalenecarboxamide.

33. A compound of claim 1 which is trans-N-(1-cyclohexyl-4-hydroxypyrrolidin-3-yl)-N-methyl-1-naphthalenecarboxamide hydrochloride.

34. A compound of claim 1 which is trans-4-chloro-N-(1-cyclohexyl-4-hydroxy-3-pyrrolidinyl)-N-methylbenzamide.

35. A compound of claim 1 which is trans-4-chloro-N-(1-cyclohexyl-4-hydroxy-3-pyrrolidinyl)-N-methylbenzamide hydrochloride.

36. A compound of claim 1 which is trans-1-ethyl-4-methylamino-3-pyrrolidinol.

37. A compound of claim 1 which is trans-1-ethyl-4-methylamino-3-pyrrolidinol ethanedioate (2:3).

38. A compound of claim 1 which is trans-4-chloro-N-(1-ethyl-4-hydroxy-3-pyrrolidinyl)-N-methylbenzamide.

39. A compound of claim 1 which is trans-N-(1-ethyl-4-hydroxy-3-pyrrolidinyl)-N-methylbenzamide.

40. A compound of claim 1 which is trans-N-(1-ethyl-4-hydroxy-3-pyrrolidinyl)-N-methylbenzamide hydrochloride.

41. A compound of claim 1 which is trans-N-(1-ethyl-4-hydroxy-3-pyrrolidinyl)-N-methyl-4-nitrobenzamide.

42. A compound of claim 1 which is trans-4-amino-N-(1-ethyl-4-hydroxy-3-pyrrolidinyl)-N-methylbenzamide.

43. A compound of claim 1 which is trans-1-ethyl-4-[(diphenylmethyl)amino]-3-pyrrolidinol.

44. A compound of claim 1 which is trans-1-ethyl-4-3-pyrrolidinol di(Z)-butenedioate.

45. A compound of claim 1 which is trans-1-ethyl-4-[(2-phenylethyl)amino]-3-pyrrolidinol.

46. A compound of claim 1 which is trans-1-ethyl-4-[(2-phenylethyl)amino]-3-pyrrolidinol di-Z-butenedioate.

47. A compound of claim 1 which is trans-N-(1-ethyl-4-hydroxy-3-pyrrolidinyl)-N-(2-phenylethyl)benzamide.

48. A compound of claim 1 which is trans-1-ethyl-4-phenylamino-3-pyrrolidinol.

49. A compound of claim 1 which is trans-1-ethyl-4-phenylamino-3-pyrrolidinol dihydrochloride.

50. A compound of claim 1 which is trans-4-chlorobenzoic acid ester with 4-[(4-chlorobenzoyl)(phenyl)amino]-1-ethyl-3-pyrrolidinol.

51. A compound of claim 1 which is trans-4-chlorobenzoic acid ester with 4-[(4-chlorobenzoyl)(phenyl)amino]-1-ethyl-3-pyrrolidinol (E)-2-butenedioate.

52. A compound of claim 1 which is trans-4-chloro-N-(1-ethyl-4-hydroxy-3-pyrrolidinyl)-N-phenylbenzamide.

53. A compound of claim 1 which is trans-4-chloro-N-(1-ethyl-4-hydroxy-3-pyrrolidinyl)-N-phenylbenzamide fumarate.

54. A compound of claim 1 which is trans-N-(1-ethyl-4-hydroxy-3-pyrrolidinyl)-N-phenylbenzamide.

55. A compound of claim 1 which is trans-N-(1-ethyl-4-hydroxy-3-pyrrolidinyl)-N-phenylbenzamide (E)-2-butenedioate.

56. A compound of claim 1 which is trans-1-ethyl-4-({2-[3,4-bis(phenylmethoxy)phenyl]ethyl}amino)-3-pyrrolidinol.

57. A compound of claim 1 which is trans-1-ethyl-4-({2-[3,4-bis(phenylmethoxy)phenyl]ethyl}amino)-3-pyrrolidinol di-(Z)-butenedioate.

58. A compound of claim 1 which is trans-1-ethyl-4-[(10,11-dihydro-5H-dibenzo[a,d]cyclohepten-5-yl)amino]-3-pyrrolidinol.

59. A compound of claim 1 which is trans-1-ethyl-4-[(10,11-dihydro-5H-dibenzo[a,d]cyclohepten-5-yl)amino]-3-pyrrolidinol(Z)-butenedioate (9:4).

60. A compound of claim 1 which is cis-4-(chloro-N-(1-cyclohexyl-4-hydroxy-3-pyrrolidinyl)benzamide.

61. A compound of claim 1 which is cis-N-(1-cyclohexyl-4-hydroxy-1-pyrrolidinyl)benzamide.

62. A compound of claim 1 which is cis-1-cyclohexyl-4-[(phenylmethyl)amino]-3-pyrrolidinol.

63. A compound of claim 1 which is cis-N-(1-cyclohexyl-4-hydroxy-1-pyrrolidinyl)-4-nitrobenzamide.

64. A compound of claim 1 which is cis-4-amino-N-(1-cyclohexyl-4-hydroxy-3-pyrrolidinyl)benzamide.

65. A compound of claim 1 which is cis-4-acetylamino-N-(1-cyclohexyl-4-hydroxy-3-pyrrolidinyl)benzamide.

66. A compound of claim 1 which is trans-4-n-butylamino-1-ethyl-3-pyrrolidinol.

67. A compound of claim 1 which is trans-4-cyclohexylamino-1-ethyl-3-pyrrolidinol.

68. A compound of claim 1 which is trans-4-chlorobenzoic acid ester with 4-[(4-chlorobenzoyl)(n-butyl)amino]-1-ethyl-3-pyrrolidinol.

69. A compound of claim 1 which is trans-4-chlorobenzoic acid ester with 4-[(4-chlorobenzoyl)(cyclohexyl)amino]-1-ethyl-3-pyrrolidinol.

70. A compound of claim 1 which is trans-4-chlorobenzoic acid ester with 4-[(4-chlorobenzoyl)(cyclohexyl)amino]-1-ethyl-3-pyrrolidinol fumarate [1:1].

71. A compound of claim 1 which is trans-benzoic acid ester with 4-[(benzoyl)(cyclohexyl)amino]-1-ethyl-3-pyrrolidinol.

72. A compound of claim 1 which is trans-benzoic acid ester with 4-[(benzoyl)(cyclohexyl)amino]-1-ethyl-3-pyrrolidinol fumarate [1:1].

73. A compound of claim 1 which is trans-4-[(4-chlorobenzoyl)(n-butyl)amino]-1-ethyl-3-pyrrolidinol.

74. A compound of claim 1 which is trans-4-[(benzoyl)(cyclohexyl)amino]-1-ethyl-3-pyrrolidinol.

75. A compound of claim 1 which is trans-4-[(benzoyl)(cyclohexyl)amino]-1-ethyl-3-pyrrolidinol fumarate [1:1].

76. A compound of claim 1 which is trans-4-[(4-chlorobenzoyl)(cyclohexyl)amino]-1-ethyl-3-pyrrolidinol.

77. A compound of claim 1 which is trans-4-[(benzoyl)(n-butyl)amino]-1-ethyl-3-pyrrolidinol.

78. A compound of claim 1 which is trans-benzoic acid ester with 4-1-ethyl-3-pyrrolidinol.

79. A compound of claim 1 which is trans-4-[(benzoyl)(n-butyl)amino]-1-ethyl-3-pyrrolidinol fumarate [1:1].

80. A method of treating depression in animals which comprises administering to said animal an effective amount of a compound having the formula:

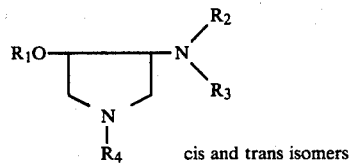

cis and trans isomers wherein;

$R_1$ is hydrogen, loweralkyl or phenylcarbonyl, $R_2$ is hydrogen, loweralkyl, lowercycloalkyl, phenyl or phenylloweralkyl, $R_3$ is hydrogen, loweralkyl, phenylloweralkyl, phenylcarbonyl, diphenylmethyl, -5-yl-10,11-dihydro-5H-dibenzo[a,d]cycloheptane, or naphthyl-carbonyl, $R_4$ is hydrogen, loweralkyl, phenylloweralkyl or lowercycloalkyl, Phenyl is unsubstituted phenyl or phenyl substituted by 1 to 3 groups selected from halogen, alkyl, loweralkoxy, trifluoromethyl, benzyloxy, nitro, amino, acetamido, and hydroxy, or the pharmaceutically acceptable acid addition salts thereof.

81. A method of claim 80 wherein the compound used is trans-4-chlorobenzoic acid ester with 4-[(4-chlorobenzoyl)(phenyl)amino]-1-ethyl-3-pyrrolidinol.

82. A method of claim 80 wherein the compound used is trans-4-chlorobenzoic acid ester with 4-[(4-chlorobenzoyl)(phenyl)amino]-1-ethyl-3-pyrrolidinol fumarate.

83. A method of claim 80 wherein the compound used is trans-4-chloro-N-(1-ethyl-4-hydroxy-3-pyrrolidinyl)-N-phenylbenzamide.

84. A method of claim 80 wherein the compound used is trans-4-chloro-N-(1-ethyl-4-hydroxy-3-pyrrolidinyl)-N-phenylbenzamide fumarate.

85. A method of claim 80 wherein the compound used is trans-N-(1-ethyl-4-hydroxy-3-pyrrolidinyl)-N-phenylbenzamide.

86. A method of claim 80 wherein the compound used is trans-N-(1-ethyl-4-hydroxy-3-pyrrolidinyl)-N-phenylbenzamide fumarate.

87. A pharmaceutical composition for treating depression in animals comprising (a) an effective amount of a compound of the formula:

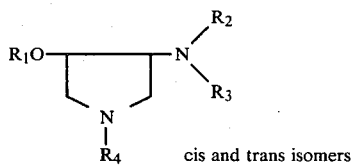

wherein;

R₁ is hydrogen, loweralkyl, or phenylcarbonyl,

R₂ is hydrogen, loweralkyl, lowercycloalkyl, phenyl or phenylloweralkyl,

R₃ is hydrogen, loweralkyl, phenylloweralkyl, phenylcarbonyl, diphenylmethyl, -5-yl-10,11-dihydro-5H-dibenzo[a,d]cycloheptene, or naphthyl-carbonyl, R₄ is hydrogen, loweralkyl, phenylloweralkyl or lowercycloalkyl, Phenyl is unsubstituted phenyl or phenyl substituted by 1 to 3 groups selected from halogen, alkyl, loweralkoxy, trifluoromethyl, benzyloxy, nitro, amino, acetamido, and hydroxy, and (b) a pharmaceutically acceptable carrier therefor.

88. A pharmaceutical composition of claim 87 wherein the compound is trans-4-chlorobenzoic acid ester with 4-[(4-chlorobenzoyl)(phenyl)amino]-1-ethyl-3-pyrrolidinol.

89. A pharmaceutical composition of claim 87 wherein the compound is trans-4-chlorobenzoic acid ester with 4-[(4-chlorobenzoyl)(phenyl)amino]-1-ethyl-3-pyrrolidinol fumarate.

90. A pharmaceutical composition of claim 87 wherein the compound is trans-4-chloro-N-(1-ethyl-4-hydroxy-3-pyrrolidinyl)-N-phenylbenzamide.

91. A pharmaceutical composition of claim 87 wherein the compound is trans-4-chloro-N-(1-ethyl-4-hydroxy-3-pyrrolidinyl)-N-phenylbenzamide fumarate.

92. A pharmaceutical composition of claim 87 wherein the compound is trans-N-(1-ethyl-4-hydroxy-3-pyrrolidinyl)-N-phenylbenzamide.

93. A pharmaceutical composition of claim 87 wherein the compound is trans-N-(1-ethyl-4-hydroxy-3-pyrrolidinyl)-N-phenylbenzamide fumarate.

* * * * *